(12) United States Patent
Raghavan et al.

(10) Patent No.: US 8,249,813 B2
(45) Date of Patent: Aug. 21, 2012

(54) SYSTEM AND PROCESS FOR METABOLIC GUIDANCE OF INTRODUCED CELLULAR MATERIAL

(75) Inventors: Raghu Raghavan, Baltimore, MD (US); Timothy Poston, Singapore (SG)

(73) Assignee: Brainlab AG, Feldkirchen (DE)

(*) Notice: Subject to any disclaimer, the term of this patent is extended or adjusted under 35 U.S.C. 154(b) by 3228 days.

(21) Appl. No.: 10/442,989

(22) Filed: May 22, 2003

(65) Prior Publication Data

US 2004/0236554 A1 Nov. 25, 2004

(51) Int. Cl.
G01N 33/48 (2006.01)
G01N 33/50 (2006.01)
G01N 31/00 (2006.01)
G06F 7/60 (2006.01)
C12Q 1/00 (2006.01)

(52) U.S. Cl. .................. 702/19; 702/22; 702/27; 703/2; 435/4

(58) Field of Classification Search .................. None
See application file for complete search history.

(56) References Cited

U.S. PATENT DOCUMENTS

| 5,964,705 A | 10/1999 | Truwit et al. |
| 6,026,316 A | 2/2000 | Kucharczyk et al. |
| 6,549,803 B1 | 4/2003 | Raghavan et al. |
| 6,801,859 B1 * | 10/2004 | Friend et al. ............... 702/19 |

FOREIGN PATENT DOCUMENTS

| EP | 0 702 966 A2 | 3/1996 |
| WO | 00/71169 A2 | 11/2000 |
| WO | WO 01/85230 A2 * | 11/2001 |

OTHER PUBLICATIONS

Souders et al. Tracheal gas exchange: perfusion-related differences in inert gas elimination. Journal of Applied Physiology, vol. 79, 1995, pp. 918-928.*

Chen et al. Intraparenchymal drug delivery via positive-pressure infusion: experimental and modeling studies of poroelasticity in brain phantom gels. IEEE Transactions on Biomedical Engineering, vol. 49, Feb. 2002, pp. 85-96.*

Venter et al. A comparative study of an in situ adapted diffusion cell and an in vitro Franz diffusion cell method for transdermal absorption of doxylamine. European Journal of Pharmaceutical Sciences, vol. 13, 2001, pp. 169-177.*

Tsuchihashi et al. Development of a pharmacokinetic/pharmacodynamic (PK/PD) simulation system for doxrubicin in long circulating liposomes in mice using peritoneal P388. Journal of Controlled Release, vol. 61, 1999, pp. 9-19.*

Nosovitsky et al. Computers and Biomedical Research, vol. 30, 1997, pp. 61-82.*

* cited by examiner

*Primary Examiner* — Russell S Negin
(74) *Attorney, Agent, or Firm* — Renner, Otto, Boisselle & Sklar, LLP

(57) ABSTRACT

A computer-implemented system and method for determining an optimal manner of introducing and moving an introduced entity from an introduction site to a target tissue region. The method comprises: calculating a modeling value at the introduction site, the pathway to the target tissue region, and the target tissue region; calculating a diffusion value representing a concentration gradient of the introduced entity as it moves through the introduction site, the pathway, and the target tissue region; calculating a flow value representing how the introduced entity is transported through the introduction site, the pathway, and the target tissue region; and determining a time, location, and method for introducing and moving the introduced entity based on the modeling value, the diffusion value, and the flow value.

52 Claims, 6 Drawing Sheets

SYSTEM AND PROCESS FOR METABOLIC GUIDANCE OF INTRODUCED CELLULAR MATERIAL

BACKGROUND OF THE INVENTION

1. Field of the Invention

The present invention relates generally to the field of controlling the activity of cells introduced in tissue, and specifically to metabolically guiding cells introduced in tissue.

2. Background of the Technology

Metabolic engineering manipulates the rate of chemical reactions (i.e., chemical kinetics) in stirred cell populations to increase or decrease the production of desired substances. Where it is critical to the pathway of a metabolite that a certain process happen in a certain cell structure (e.g., a vacuole), that cell structure is treated as an extensionless compartment. In a larger environment, such as a stirred tank (i.e., a stirred cell population environment), maximum productivity occurs with each cell in the optimum state. The cells are also assumed to be homogeneous. When the cells are not homogeneous, the metabolic engineering is analyzed in terms of homogeneous cells and the extracellular metabolites within a uniform environment, and implied spatial variation is not brought into the kinetic analysis. Metabolic engineering manipulation is performed by: 1) genetic modification; and 2) modification of the stirred cell tank concentration of entities which affect the core kinetic processes (e.g., heat, nutrients, and waste products) or the kinetics regulatory logic (e.g., signaling compounds). For numerous cells, it is possible to apply genetic modifications for desired goals and to control the behavior of the cells. For example, it is possible to control a cell so as to cause it to multiply rapidly until it has reached an optimum level, and then divert its resources to produce, rather than grow, a desired compound. Such control involves delivering a specific molecular signal to the cell, which responds (either naturally or by genetic engineering) to that signal in a specific way.

Several types of activity are of interest in metabolic engineering. These include, but are not limited to: production (e.g., of genes, protein), secretion (i.e., production by a cell of a substance and its introduction into the body), proliferation (i.e., growth and reproduction of similar cells), and apoptosis (i.e., programmed cell death). (The term "introduction" refers to all methods and devices of delivery of any transportable entity from outside, including but not limited to: infusion, perfusion, retro perfusion, injections, and electromagnetic or ultrasound radiation. Where blood pressure or temperature is lowered by an extraction process, this is referred to as introduction of a negative quantity.) These activities must be managed over time. For example, initial rapid proliferation achieves a large population of cells, but at the optimum productive density (not necessarily the level at which proliferation is blocked by crowding or nutrient shortage), one wishes to turn their activity to production of the desired compound. All of these activities are significant also for cells introduced into a subject. For example, hypothermia (lowered temperature) can improve survival rates in implanted cells.

The metabolic engineer may wish to know and potentially control the following issues:

Whether the cells will remain close to the introduction point, how far they will spread through a target or dissipate beyond it, and whether they can migrate in sufficient quantity from a selected introduction point to a desired target point.

Whether the cells form multicellular masses that resist passive transport.

Whether the cells will attach themselves before arriving in a desired target region, preventing such arrival, or fail to attach themselves at the desired target region.

Whether and at what rate introduced cells may attack other cells (as T-cells and sometimes stem cells do naturally); how genetic engineering might be targeted to the destruction of cell types not already attacked by the subject's own cells (e.g., cancer cells or fat cells), while avoiding cells where attack is undesired or acting in a sustaining fashion for other cells (e.g., becoming oligodendrocytes replacing the myelin sheath for neurons that have lost them in such disorders as multiple sclerosis); providing trophic (nutritional) support for other cell types introduced in a procedure; or exchanging genetic material with other cells, modifying their function by in vivo genetic engineering.

Whether and at what rate the cells act to modify the extracellular matrix (ECM), laying down or removing proteins (e.g., collagen and elastin) in structures (e.g., skin and arteries), for which biomechanical properties change conspicuously with age; altering bone either in density (as in osteoporosis or its reversal) or in shape (as in the long-term response to mechanical loads).

Whether introduced stem cells or multipotent cells specialize to function as nerve cells in a region where this may be desired, or in a region where added neural activity might be disruptive.

Whether neural cells intended to replace cells lost or damaged (e.g., through stroke or degenerative disease) will form appropriate links.

Cell mobility, which can be ignored in a stirred tank.

Adhesion between cells of the type used, though this may affect aggregation, with positive or negative impact on production of the target compound.

Adhesion to other cell types or to an ECM, absent in a stirred tank, though a stabilizing porous matrix may be of use industrially.

Modification of the state or behavior of other cell types.

Modification of the ECM, by addition or subtraction of material.

Differentiation into other cell types.

Creation of synaptic connections.

3. Related Art

Control of Cell Mobility. The system and method as discussed in U.S. Pat. No. 6,549,803, entitled "Method and Apparatus for Targeting Material Delivery to Tissue" (hereinafter referred to as "Targeting"), incorporated herein by reference, characterized a molecular population and a cell as free or bound. A free cell is not attached to the ECM. A bound cell is attached to the ECM. The present invention considers a cell as mobile. Cell mobility includes two forms: swimming and crawling. In many cases, chemically controlling swimming is performed by causing the cell to swim straight and then tumble. Tumbling is less frequent when there is an increase in the concentration of a compound to whose source the cell usually swims (e.g., a nutrient or attractant molecule). Thus, chemotaxis (i.e., the movement of cells in response to chemicals) offers a natural path that can be controlled by manipulating chemicals. Detailed modeling of metabolic control has recently been clarified, allowing more perfect control of factors, such as speed and re-engineering of the signals detected by the cell.

Swimming occurs at a characteristic velocity relative to the ambient fluid. Thus, the presence of flow due to introduction or other causes (e.g., diffusion, random walks) must be combined with flow velocity, as explained in "Targeting". Swimming is strongly affected by the penetrability of the surrounding cells, including their anisotropy (i.e., not having properties that are the same in all directions). Thus, swimming in cross-channel directions is often more interrupted than swims along channels. Swimming can be modeled by diffusion in the presence of a tensor field of penetrability, as is described in "Targeting". If introduced cells mutually adhere to form clumps, the cells become less free to swim, and are less able to travel passively through a porous environment of limited pore size.

In crawling, a cell stays attached to the ECM, making ambient current less relevant. Crawling involves substrate adhesion molecules, which affect movement of cells and transformations of cell states. Chemotaxis (i.e., movement of organisms in response to chemicals) may be treated by a diffusion model, though characteristic speeds are lower, and the influence of the surrounding tissue on penetrability in different directions is mediated by different physics and yields different tensors for this form of transport, which must therefore be treated separately.

Control of Cell Transport and Density. Because cells are more productive in aggregated masses, the possibility of inducing cells to form masses, rather than creating masses by manipulating environmental factors, has been discussed.

In contrast, the assumption of spatial uniformity is strikingly false. When cells are introduced into the brain, the stirred brain assumption is clearly inappropriate. Cells are typically injected or otherwise introduced via a needle or catheter. The hope is that the introduced cells will move passively, carried by the injection medium, or actively, through their own mobility—to specific regions where they are needed, and not elsewhere. In the case where the introduction device carries them to the center of the target region, the hope is that the cells will spread through a significant part of that region, and will not, in too large a proportion, migrate further. The same observation applies to the introduction of dissolved or suspended molecules, or of any other active material.

Control of Other Cell Activities. Metabolic models also impact the description and control of other cell activities, such as attack, support, or genetic modification of other cells, all of which involve sustained contact. The metabolic kinetics of differentiation (having a characteristic that is different from the original) are also under widespread study, and appear increasingly open to external control by hormones, growth factors, and other molecules that one may opt to diffuse in the course of a procedure. Unlike the industrial case, differentiation appears to be essential in many therapeutic cell introductions. The fact that cells of a maturely defined type rarely embed themselves successfully in a new environment is basic to the current emphasis on stem cells for injection. It is unlikely, however, that the target environment will always provide the stimulus for the precise transformations desired of the cells. The modification of in vitro differentiation, according to the coordinated administration of factors such as vascular endothelial growth factor (VEGF) and platelet derived growth factor subtype BB (PDGF-BB), show that the metabolic understanding needed for in vivo control can be expected as the field matures.

It is important to include heat in such a modeling system for prediction and control, not only because much metabolic kinetics is naturally modified by temperature so that cellular implant protocols already address the global temperature of the patient, but because genetic engineering permits the installation of temperature-dependent switches in kinetic pathways, governing any activity for which kinetics is sufficiently understood. Cells have been created that proliferate freely at 33° Celsius, but cease to proliferate at normal body temperature, shifting to a differentiated state. Temperature is used as a global, position-independent switch, but mild local heating is among the least invasive of measures available to the clinician. (For example, focused electromagnetic energy has been used and can result in no damage to tissues nearer the surface.)

Manipulation of the temperature field can become a powerful method of control of the activity of introduced cells that are known to respond, naturally or by arrangement, in predictable ways to differences or gradients in temperature.

In spite of the many applications of the above procedures, there has been little development of explicit numerical models for the transport and evolving density of introduced material. "Targeting" addresses the logical and implementation form of some such models and specifies particular procedures for their use in control of the delivery process.

Such developments in metabolic engineering indicate it will be increasingly practical to fine tune cell behavior over time and trigger substantial changes in cell behavior in the implantation context. The search for effective cell treatment will involve increasingly complex planning in space and time. In fact, planning in space and time has already been found useful in laboratory studies to improve implanted cell survival by including apoptosis inhibitors, antioxidants (an agent that inhibits the deterioration of materials through oxidation), and trophic factors (nutrition factors) in the introduced material. In addition, it has been found useful to bring the region below normal blood temperature during a period starting with the injection. This creates a larger search space in which to find an optimal therapy, making it unwise to rely on the best method being among those tried early. The search space will become larger again when (as we predict) the coordinated time-variation of inputs becomes necessary, and the spatial distribution of cells receives closer attention. For example, there is current debate over whether dopaminergic cells placed in the putamen suffice in treating Parkinson's, or whether they should go also to the striatum and/or the substantia nigra. The greater depth of the substantia nigra complicates the surgical procedure of direct implantation, and such multiple direct placement increases incidental damage to the brain. It is thus preferable to inject cells at a more easily and safely accessible point, in such a way that they will migrate to the actual target tissue(s). There are already instances of this approach, with cells that "know where they belong" injected with little regard for location, and migrating to the most useful place, but successes with this position-independent approach are like surface nuggets. For example, an embryonic cell 'belongs', strictly, at a location in an embryo. In the adult patient, acting accordingly can cause complications (e.g., in the neural connections it forms). To expect all cell types that can usefully be implanted to know where they will be therapeutically useful, and go there, is unsustainable optimism.

Thus, although it is known that neural stem cells migrate preferentially to the site of an ischemic injury (e.g., in the rat), there is a need to inject exogenous stem cells to augment the brain's own response to attempt to heal the injury, and also a need to organize and optimize this response. The present invention includes a specific approach to guiding cells and trophic/tropic factors to this end. For example, with ischemic stroke, there are compelling reasons not to transplant cells and attendant factors directly into the focal region of ischemia, due to already-present injury. As another example, one could therapeutically disrupt the blood-brain barrier (BBB), or utilize regions of the brain where the BBB is naturally modified (e.g., circum-ventricular structures) to inject materials that would otherwise be unable to penetrate brain tissue into the blood stream with a view to cure injured cells or tissue in the brain. It is important to know, and to be able to guide, the injected material to the specific locations where their therapeutic action is needed and effective.

In another example, neurotropic and neurotrophic factor pharmacology can be utilized. As spatial distribution information is available, the proper guidance of factors, as well as cells, will become critical. For example, Peptide (PACAP) is distributed within the brain parenchyma in the adult rat, while its receptors are principally located in the ventricular and sub-ventricular zones. This type of distribution and location issue is likely to be a common influence on factors needed for proper development. Thus, guiding the factors to the proper receptor locations is needed so that PACAP can function as a valuable neuroprotective agent.

If one needs to direct cells, the design of a procedure becomes more complex. Signaling compounds injected before, during, or after the cell introduction (e.g., from the same locus or other loci, using a less-invasive catheter or finer needle than required for cell delivery) may guide the cells to the desired target. It is clearly useful for the cells to be mobile when first introduced, but in the target area, the cells should attach themselves and devote resources to producing the material (e.g., dopamine) intended for that target. If a molecular agent that in a certain concentration range will trigger such a behavioral change diffuses faster (as is typical) than cells travel, it can be released from the same introduction point at an appropriate time later, to cause the majority of introduced cells to encounter a concentration of that agent in the appropriate range when they are in the appropriate region. Similarly the activity of the cells may be required for a limited time (e.g., to promote a form of healing or regrowth) or for a particular purpose (e.g., to attach themselves to a tumor and produce cytotoxic material to which cancer cells are particularly sensitive). At a certain time, such cells' work is completed, and it is preferable for them to disappear. If they do not recognize (e.g., naturally or by engineering/programming of their metabolism) the completion of their tasks and respond by apoptosis, then a molecular signal should be sent which causes them to do so. The delivery of this signal in an appropriate concentration, again, may require significant control. For example, especially in conjunction with coil design, the introduction of transcranial magnetic stimulation (TMS) allows focused delivery of electrical stimulation of particular brain regions. When appropriate cells and factors have been guided to locations, such radiative input may be used to control the rate of particular activities and pathways. The design of such multiple delivery over time and space of a plurality of cellular and molecular agents, whether fully tailored for the individual patient or as a protocol with or without some customization parameters, requires systematic model-based planning.

Image guidance permits a user injecting a substance to place a delivery instrument (e.g., a catheter) into a location (e.g., a human brain) and visualize the instrument's location relative to scan-visible structures. In present cell delivery practice, the user makes a plan for injection. This plan for injection includes the following steps: determining the composition of the cell suspension and the quantity to be loaded into the delivery system; determining the pressure or flow rate (perhaps variable) at which the substance is to be injected; and determining the time over which the flow is to be maintained. The objective of such a plan for injection is to deliver the cells in desired quantities in or to 'target' tissues, often while minimizing the number delivered to non-target and vulnerable tissues. Non-target tissues are tissues where the cells would be wasted, and vulnerable tissues are tissues where the cells would do harm. It is also desirable to limit excess pressure and the resulting edema (swelling) of tissue, in spatial extent, intensity, and duration.

Commonly, the plan is entered into a computer that will control the injection process, but direct hand control is also possible. The developed plan is then followed, with a change only if visually inspected images of the diffusing substance makes clear that concentration, pressure or edema is not following the course expected by the user. See, e.g., U.S. Pat. Nos. 6,026,316 and 5,964,705, which are hereby incorporated by reference. Since the evolving concentration is a three dimensional (3D) scalar field in the midst of complex 3D structures, visual inspection requires a strong grasp of the 3D relationships revealed by scan data. The prior art is limited, in that its 3D display techniques do not display these relationships clearly enough to guarantee fast comprehension and appropriately swift action by the medical user. It is rare that undesired consequences are seen fast enough to limit their scope. There is an unmet need for better 3D display techniques.

"Targeting" replaces or augments such visual inspection by enabling the computer to monitor this part of the control loop. At the simplest level of control in the invention of "Targeting", the user chooses a position or target area and specifies an introduction plan (quantity, duration, pressure/flow-rate) to the computer. The computer then solves or determines the transport properties, on the assumption that this plan is followed, using a field of parameters P, together with available subsidiary data, such as blood pressure, to specify boundary conditions. The system displays the predicted values of concentration, pressure and edema, and the user has the opportunity to examine them at non-crisis speed, so as to determine whether they are satisfactory. If not, the user repeatedly changes the device position (actually or virtually) and/or the specified plan until an acceptable result is predicted. At this point, the plan is implemented under computer control.

SUMMARY OF THE INVENTION

The present invention solves the deficiencies of the prior art, as well as others, by providing a computer-implemented system and method of introducing (e.g., injecting) and moving an introduced entity to an organism from an introduction site to a target tissue region.

In one embodiment, the present invention provides a computer-implemented system and method for determining at least one manner of introducing and moving at least one introduced entity from an at least one introduction site to at least one target tissue region in an organism, comprising: calculating at least one modeling value at the at least one introduction site, at least one pathway to the target tissue region, and the at least one target tissue region; calculating at least one biological activity value representing an interaction between the at least one introduced entity and the introduction site, the pathway, and the target tissue region; calculating at least one diffusion value representing a concentration gradient of the at least one introduced entity as it moves through the introduction site, the pathway, and the target tissue region; calculating at least one flow value representing how the at least one introduced entity is transported through the introduction site, the pathway, and the target tissue region; and determining at least one time, location, and method for introducing and moving the at least one introduced entity based at least on the modeling, the at least one biological activity value, the at least one diffusion value, and the at least one flow value.

In another embodiment, the present invention provides a system and method for intraparenchymally administering at least one introduced entity to at least one target tissue region in an organism, comprising: introducing the at least one introduced entity in at least one intraparenchymal introduction site apart from the target tissue region; and moving the at least one introduced entity from the at least one intraparenchymal introduction site to the at least one target tissue region.

Additional advantages and novel features of the invention will be set forth in part in the description that follows, and in part will become more apparent to those skilled in the art upon examination of the following or upon learning by practice of the invention.

DESCRIPTION OF THE INVENTION

For convenience, the local density of any transportable entity is referred to herein interchangeable as a "concentration", including in some examples in which the local density may be more specialized, such as "temperature" for heat, "population density" for countable individuals, or "electrical activity" for firing cells.

One embodiment of the present invention requires that the plan specify a plurality of introductions of a plurality of transportable entities. The transportable entities include internal kinetics, determinable entities, and predicted quantities (e.g., survival rates, secretion rates). The plan may be restricted to avoidance of injection into undesirable regions, or the introduction may be of non-material signals. If the resulting predicted concentrations and rates involve values pre-specified by the user as unacceptable, the computer can pause the injection for new user input. If the resulting concentrations and rates involve values specified as acceptable, the computer may then implement the procedure.

The above-described process may be used for individual patients or for research to yield standard protocols for application in clinical use. For a patient, estimation can be made of movement parameters. For research, animals or trial patients can be used to yield standard protocols.

Metabolic Cell Guidance System Overview

Figure 1:
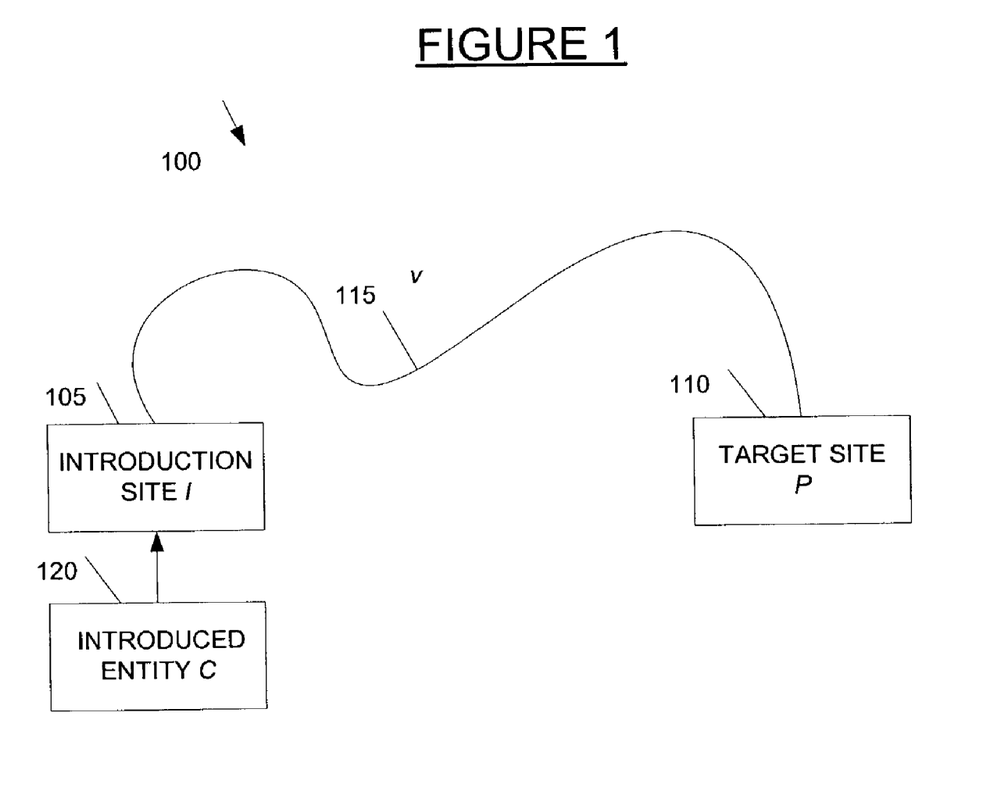
FIG. 1 is a drawing illustrating an overview of the metabolic cell guidance system, in accordance with an embodiment of the present invention.

FIG. 1 illustrates the data structure of the system in an exemplary embodiment of the present invention. The system includes these components: an introduced entity C 120, an introduction site I 105, a target site P 110, and flow velocity v 115.

In one embodiment, the system comprises a library created by the system builder. The library contains models for cell behavior. Qualitative information (e.g., on metabolic pathways, regulatory networks) has a positive influence on this portion of the cycle. In such cases, the present invention employs aspects of the qualitative theory of equations, including but not limited to, singularity, bifurcation, and catastrophe theory to derive suggested interventions, model behavior, or further experimentation to introduce quantitation where necessary. The methods alluded to allow one to organize the projected behavior around the regions (of concentrations of cells and metabolites, etc.) where abrupt changes in behavior may be expected, and where the possible types (e.g., points, higher dimensional spaces) and number of such regions can be revealed by the analyses and methods just mentioned. In some embodiments, the models are proprietary or shared. Models for desired cell behavior can also be optionally used with some embodiments. To use a model for desired cell behavior, its model for cell behavior and its specified or estimated population density are required. The method includes creating introduction plans computed to deliver appropriate concentrations of cells and materials at suitably coordinated times, using imaging to track conformity of the results with the plans, and follows procedures to modify or abort the plans where necessary.

Target Site P. In one embodiment of the present invention, the body region target site is treated as a field P of local properties (e.g., constants of diffusion, absorption and metabolic kinetics), rather than as an assembly of organs. (These local properties may vary from point to point, but are normally "constant" with respect to time, being fixed in the timescale of an introduction procedure. However, agents such as vasoconstrictors may rapidly alter diffusion characteristics, so the term "constant" is not to be understood herein in a limiting sense.)

The field P specifies, for at least one point x, each scalar, vector, or tensor quantity. The value of P at a point x is the ordered list of local property values at x. This field P may vary in time (e.g., with heart or lung motion) and in space.

Introduction Site I. In an embodiment of the present invention, the introduction site I represents the area where the introduced entity is first introduced into the organism.

Flow Velocity v. In an embodiment of the present invention, the moving fluid is defined hereby as a flow velocity field v. The moving fluid may have, for example, a steady or periodic motion due to body processes, or a transient, time-varying flow driven, for example, by a pressure difference between introduction devices, concentration variations, osmotic pressure, and background pressure in the organism. At some stage (e.g., after introduction ceases or release of the material ceases), the flow velocity v may become negligible.

Introduced Entity C. The introduced entity is introduced and moved through the organism to achieve a desired goal, such as a therapeutic effect, a cosmetic effect, a modification of performance in a mental activity, or a modification of performance in a physical activity. In addition, in determining the success with the introduced entity meeting the desired goal, the following actions may be taken: measuring secretion rates, revascularization, neural function, muscular function, tendon function, bone quality and shape, or an effect of a material on cancer cells, fat cells, extracellular matrices, membranes, lung tissue function, or cardiac function. The introduced entity includes at least one among a cellular material, a non-cellular material, and an electromagnetic stimulus. The cellular material includes, for example, dopaminergic neurons, cholinergic neurons, adrenergic neurons, serotinergic neurons, glial cells, ganglion cells, fetal stem cells, autolytic stem cells, pluripotent cells, embryonic ectoderm cells, neural crest cells, embryonic mesoderm cells, and embryonic endoderm cells. The non-cellular material includes, for example, hormones, recombinant peptides, neuropeptides, trophic/tropic factors (e.g., growth factors (e.g., platelet derived growth factor (PDGF), nerve growth factor (NGF), brain derived growth factor (BDGF), fibroblast growth factor (FGF)), glial cell line-derived neurotrophic factor (GDNF), ciliary-derived neurotrophic factor (CNTF), neurotropins, receptor tyrosine kinase agonists, receptor tyrosine kinase antagonists, pantropic neurotrophins), interleukins, cytokines (e.g., cytokeline leukemia inhibitory factor (LIF)), colony stimulating factors, caspase, marker molecules (e.g., imaging technique molecules, functional magnetic resonance imaging (MRI), positron emission tomography (PET), fluoroscopy, radionuclide imaging), and drugs. The electromagnetic stimulus includes, for example, electric current, magnetic pulse, and photon emission.

In an embodiment of the present invention, the introduced entities are defined as $C_1, \ldots, C_N$, representing concentrations of diffusing entities (e.g., heat, molecules, cells, or microscopic devices) dissolved or otherwise linked to the moving or static fluid. In one embodiment, the introduced entities are treated as influenced by, but without influence upon, the fields P of local properties and v of flow velocity.

In one embodiment, the present invention estimates P; estimates v; and then uses P and v to predict the evolution of C. In certain cases, an impact of C upon P or v does exist (e.g., where a diffusing drug stimulates a change in the mechanical properties of tissue), requiring an iterative process of improving the estimate of P or v in light of the results of C, using the result for a repeat of C, etc.

In one embodiment of the present invention, $C_i$ is the concentration of a cell type, associated with a set of fields of cellular concentration of each metabolite of interest for that cell type, and constants specifying a metabolic model. A cellular concentration is the concentration $c_j(p)$ of a molecule within a cell (or within its characteristic compartment of a cell, as in typical non-spatial metabolic models) at (p), and this concentration $c_j(p)$ travels with the cell, so that a moving, non-uniform field $c_j$ has a non-zero rate of change $\partial c_j/\partial t(p)$ at a fixed point p, even if nothing is changing in the cell. A cellular rate (e.g., for secretion) travels similarly with the cell. The molecule's mean spatial concentration at a point p is therefore proportional to $C_i(p) c_j(p)$, and a per-cell excretion rate of a particular compound through the cell membrane must be multiplied by $kC_i(p)$ to obtain the rate per milliliter at which that compound is added to the shared fluid environment, where k is a constant relating cell size to volumetric and mass units in the ambient space. Since non-static cells typically follow random walks, which mix them, rather than moving smoothly on a set of non-intersecting curved trajectories, the assumption of the existence of a mean intracell $c_j$ at a point forces a between-cells diffusion term in the evolution of the $c_j$. In another embodiment, a more precise model treats the statistical variation in cell states in each small region; in the embodiment above, this variation is neglected in the interest of computing speed. Similarly, in the above embodiment, the metabolic literature by ignoring spatial concentration variation across the interior of a cell.

An ambient interaction model specifies the kinetics of the fields $C_i(p)$, with coefficients that (unlike the $C_i(p)$ themselves) are independent of position p. Where appropriate, the terms in this model involve cellular rates of excretion and uptake, and therefore expressions of the above form $C_i(p) c_j(p)$. Relatively few compounds are exchanged between the cell and the surrounding fluid, compared to the number required in describing its internal metabolic kinetics, so that parallelization may separate computation of such kinetics from computation of the ambient interaction model without too high a penalty in communication effort.

In another embodiment of the present invention, fields of cellular concentrations may optionally be assigned to immobile cell populations that are part of the organism into which the materials are introduced. A metabolic model for a cell may be a pathway analysis, which requires fewer data to construct, and is often available earlier, but in the absence of stoichiometric constants, the model cannot predict specific rates for metabolic processes. It does however define a simplex in kinetic space in which the cell must operate, so that by attention to extremes, a numerical model distributed in space and time can yield upper and lower bounds for the activities of final interest, such as secretion of key metabolites.

The metabolic model for a cell may also be a kinetic model. The metabolic model also extends to other types of intracell modeling (e.g., including the phenomenon of internal diffusion or transport along microtubules) as sufficient detail becomes available from metabolic research and sufficient processing power from the computer industry.

Metabolic Cell Guidance Method Overview

Figure 2:
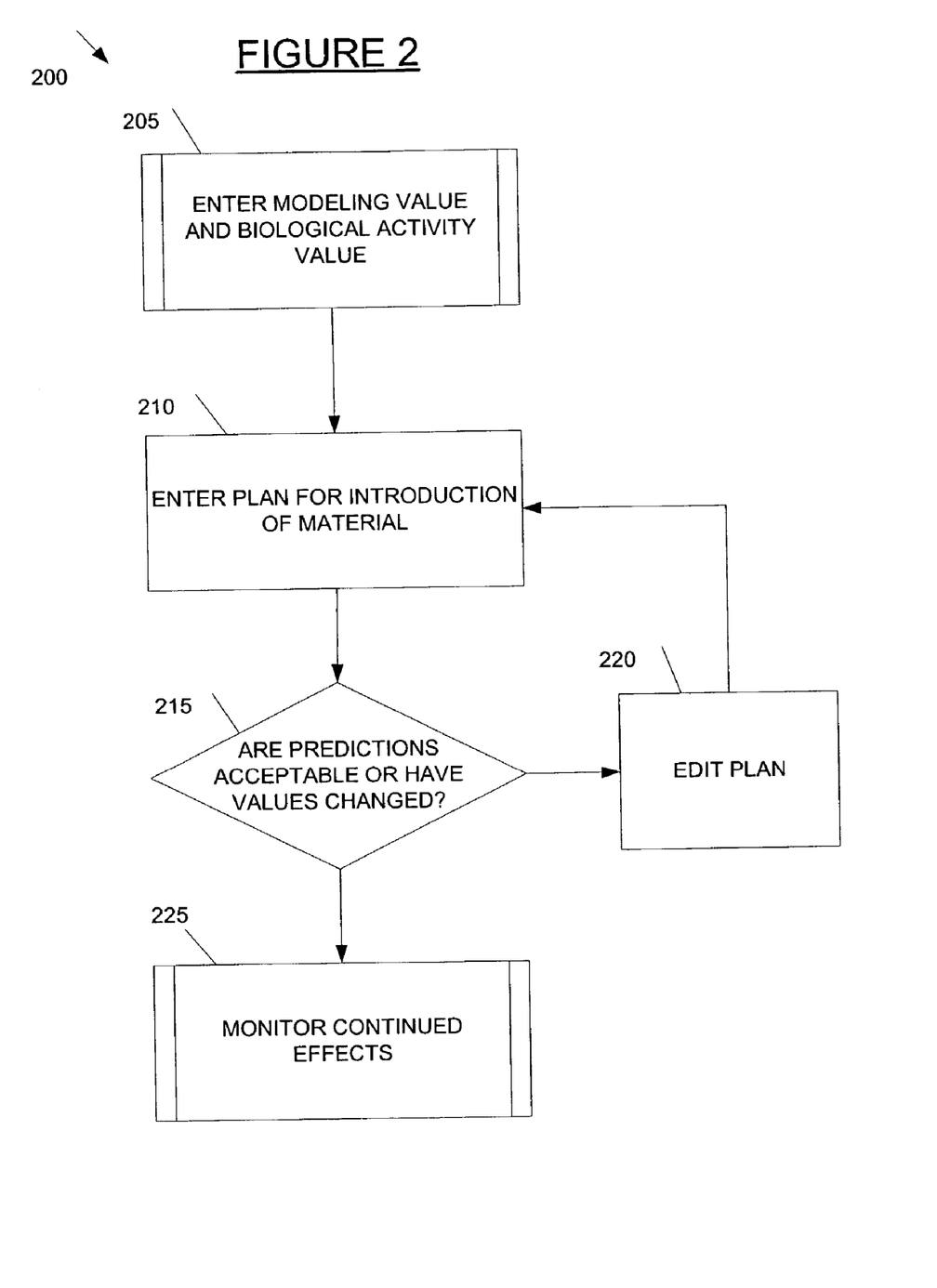
FIG. 2 is a flowchart illustrating an overview of a metabolic cell guidance method, in accordance with an embodiment of the present invention.

FIG. 2 is a flowchart 200 illustrating an overview of the method for metabolic guidance of introduced cellular material, in accordance with an exemplary embodiment of the present invention. In step 205, the modeling values and biological activity values are input, as described further with regard to FIG. 3, below.

In step 210, the values describing a plan are input, which include at least one of: introduction site or sites, flow rate or pressure difference to be enforced, settings for electromagnetic radiation, the amount and nature of entities to be introduced, and the method of introduction. In an embodiment of the present invention, the manner of introducing and moving the introduced entity is repeated a plurality of times in accordance with a numerical specification. The numerical specification can utilize standard clinical parameters. In addition, the numerical specification can be electrophysiologic, and can include transcranial stimulation or intro-parenchymal electromagnetic stimulation. The time, location, and method can be determined by using modeling, biological activity, diffusion, and flow values of the organism, or of another representative organism (e.g., an organism with characteristics similar to the organism).

In step 215, it is determined whether the predicted results for concentrations and activities (e.g., transport and activity of the cells, and of the metabolic interaction with the cells already present, where these are modeled) are acceptable or if any values assumed in step 205 have changed in the simulation, due to assumed dynamics.

In an embodiment of the present invention, the target minimum or maximum of the introduced entity at the target tissue region is specified. In another embodiment, a warning is issued if the target minima or maxima are predicted to be unmet using a planned time, location, and method. In a further embodiment, a range of possible planned times, locations, and methods are selectable, and preferential planned times, locations, and methods are identified.

In one embodiment of the present invention, the planning system is coupled to real implementation of the plan. In this embodiment, the computer or other processor-linked display includes markers for agreement with the user's goals, so that visual inspection is guided to possible regions of concern. For example, a concentration, under the assumptions of a current planned time, location, and method, can be graphically displayed. Furthermore, the target tissue region, or an optical property relative to the target tissue region, can be visualized. When a chosen plan is implemented, using scan-visibility of the real injected substance, the computer can monitor deviation from the expected time course of concentration, and detect problems earlier than visual monitoring. Where deviation beyond a threshold level is detected, the computer derives revised estimates for the transport parameters P and deduces revised predictions for the results of the plan. This can be done by displaying the information to a user so that it can be inspected, or by an automated program. For example, if 210 indicates that specific compounds can trigger the desired behavior, in step 215, the system determines whether the user has entered the specific compounds.

If the predictions are not acceptable or the values have changed, the information of step 210 is edited in step 220, and then re-assembled and re-optimized in step 210. The instrument position may be readjusted, and new values may be defined for quantity, duration, pressure/flow-rate of the injection. If these involve values pre-specified by the user as unacceptable, the computer may pause the injection for new user input. The process will then go back to step 210, recompute the predicted concentrations and activities, and then move to step 215 to see if these recomputed predictions are acceptable.

In an embodiment of the present invention, step 210 includes simulating movement of the introduced entity. The simulating includes: constructing a local physical quantity corresponding to a motion, appearance, and disappearance of the introduced entity; modeling at least one direction value at least one point in space to simulate the direction of motion of the introduced entity; computing a direction value over time; and/or modeling a metabolic interaction of an already-present entity with the introduced entity. The simulated movement includes: optimizing resulting concentrations at the target tissue area; and/or minimizing resulting concentrations at areas that are not the target tissue area.

The local physical quantity includes cell mobility, conduction, diffusion, flow, creation, destruction of molecules, and/or absorption. In one embodiment, the local physical quantity is a transport value descriptive of resistance to motion in different directions. In another embodiment, the local physical quantity is modified by a formula describing the local physical quantity's change in response to a concentration of the introduced entity.

The transport value is descriptive of cell mobility, conduction, diffusion, and/or flow. The transport value is constructed from data of a scout entity that has a property similar to a property of the introduced entity. This similar property (e.g., physical properties, chemical properties) can be constructed from: magnetic resonance data; data recorded from the previous introduction of the introduced entity; and/or data permitting segmentation of the target tissue region into anatomical types, where at least one diffusion value (e.g., concentration, motions, etc. known from actual measurements on other subjects) is known. In one embodiment, the predicted concentration is compared to an actual measured concentration to modify the field of the local physical quantity.

If the predicted concentrations and activities are acceptable, the predictions for the changed concentrations of the cells are implemented in step 225, as described further with respect to FIG. 5, below. The local properties governing the interaction of the fields $C_i(p)$ with the subject are estimated by the means described in "Targeting". In certain cases, if an impact of C upon P or ν (e.g., where a diffusing drug stimulates a change in the mechanical properties of tissue) does exist, the estimate of P or ν is improved, in light of the results of $C_i(p)$, and the result is used to recompute. This process can be performed multiple times. General properties such as intracellular metabolic kinetics, or the terms and coefficients of the ambient interaction model, are found by appropriate Experimentation in vitro, or in vivo upon other organisms than a subject of the process here described.

Enter Values

Figure 3:
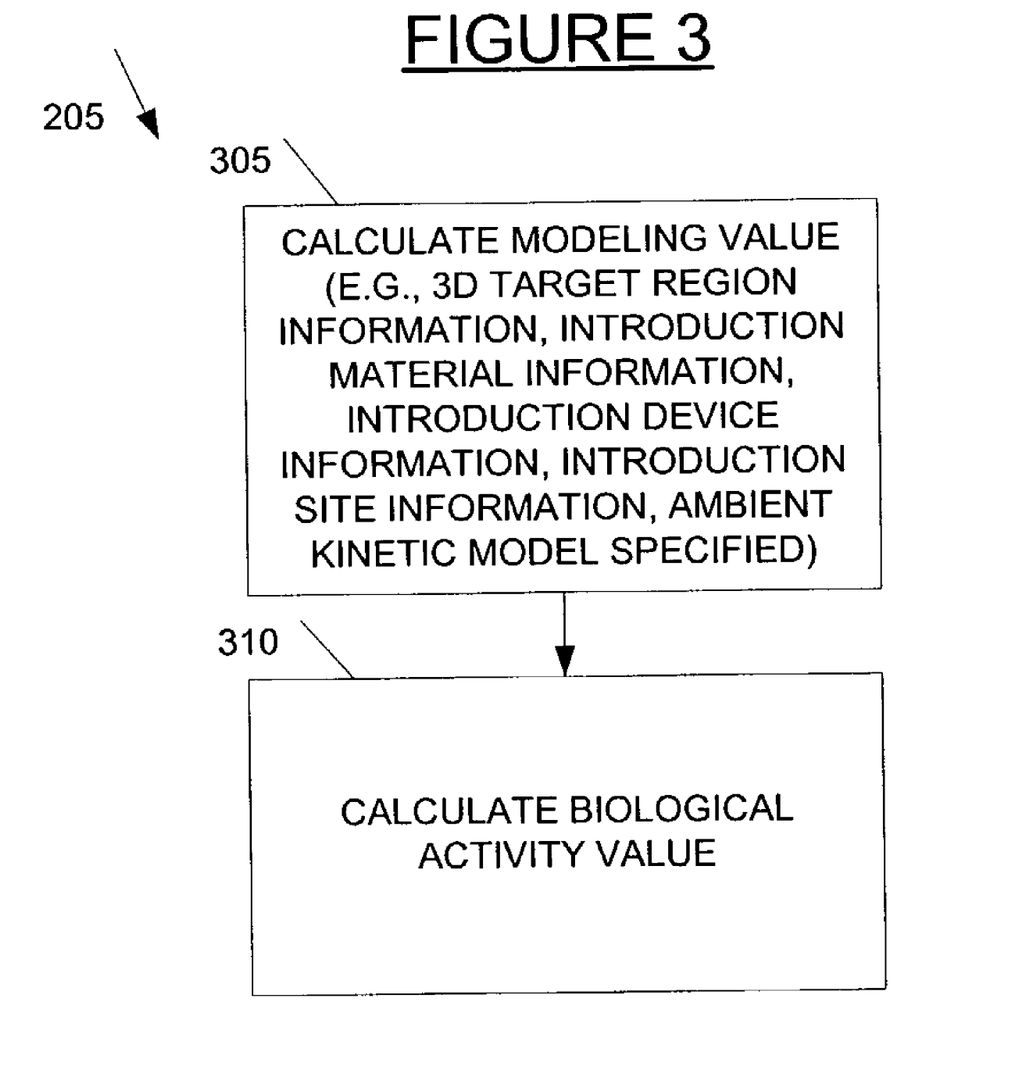
FIG. 3 is a flowchart illustrating process 205 of FIG. 2, in accordance with an embodiment of the present invention.

FIG. 3 is a flowchart illustrating entering the values as described in process 205 of FIG. 2, in accordance with an embodiment of the present invention.

In step 305, a modeling value is calculated. The modeling value is calculated at the introduction site, the pathway to the target tissue region, and the target tissue region. In an embodiment, the introduction site, the pathway, and the target tissue region are modeled as a field of at least one point representing a property. The property includes three-dimensional information, a property of a device used to introduce the entity, a value for ambient kinetic energy, a value for an amount of the introduced entity, a value for an already-present entity, or a value for an introduced scout entity. The modeling value can include functional capillary density, tissue diffusion rate, perfusion index, histological configuration, and/or extracellular matrix density.

In step 310, at least one biological activity value is inferred. The biological activity value represents an interaction between the at least one introduced entity and the introduction site, the pathway, and the target tissue region. The biological activity value can include dominant biochemical pathways, blood flow, a functional MRI, a PET scan, electrical membrane potentials, and/or cellular electrophysiologic activity.

Figure 4:
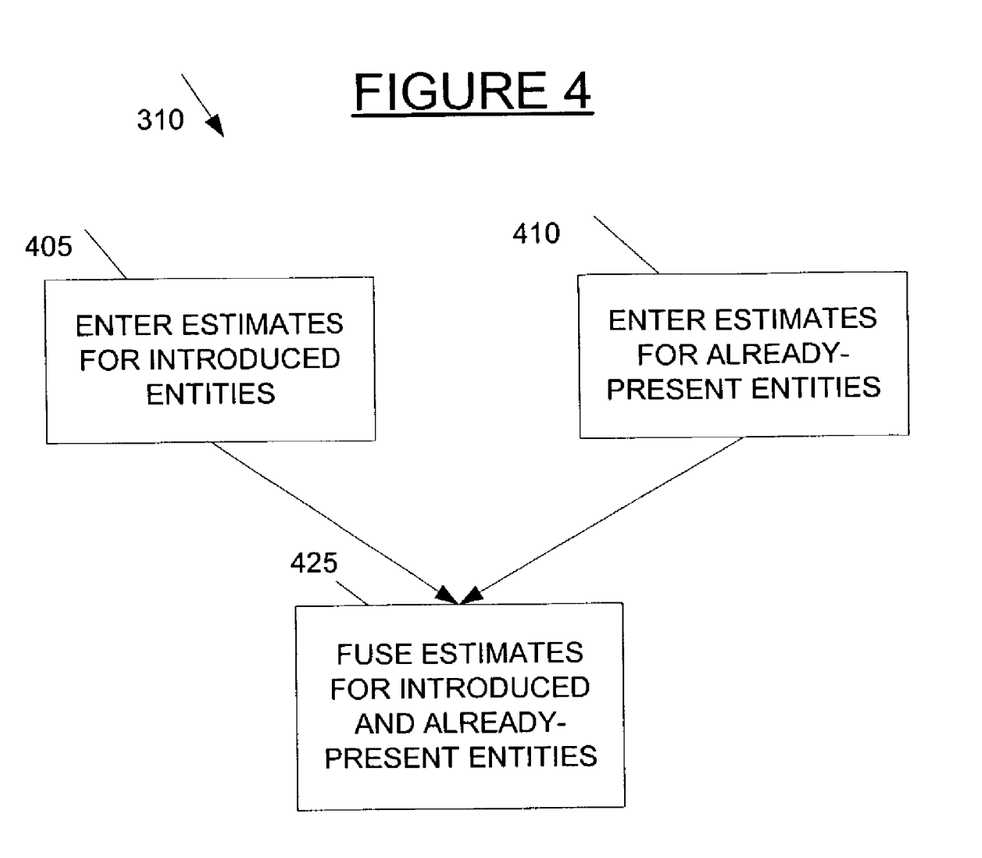
FIG. 4 is a flowchart illustrating process 310 of FIG. 3, in accordance with an embodiment of the present invention.

FIG. 4 is a flowchart illustrating process 310 of FIG. 3, where the biological value is calculated, in accordance with an embodiment of the present invention. In step 405, estimates are entered for introduced entities. Introduced entities can include surrogate entities. In step 410, estimates are entered for naturally present entities. In step 415, the estimates of 405 (if any) and 410 (if any) are fused together.

Implement Predictions

Figure 5:
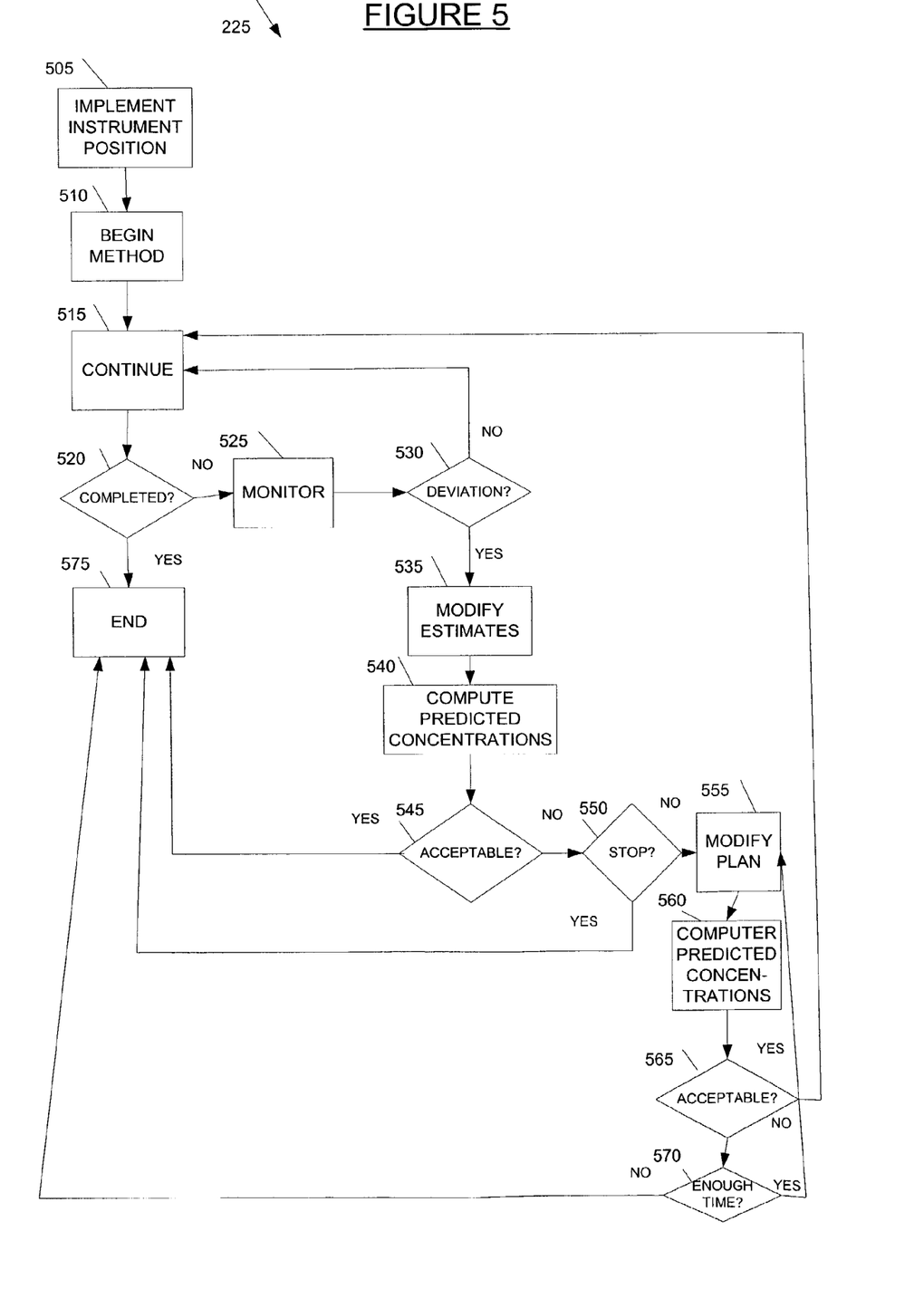
FIG. 5 is a flowchart illustrating process 225 of FIG. 2, in accordance with an embodiment of the present invention.

FIG. 5 is a flowchart illustrating implementation of the predictions process 225 of FIG. 2, in accordance with an embodiment of the present invention. In step 505, the instrument positions are implemented (if chosen virtually). If the position was chosen virtually, the instrument must first be placed there physically. In step 510, the system directs the loading of introduction devices with appropriate quantities of materials in appropriate formulations (e.g., formulations that optimize viscosity or other transport properties, and pre-treatment of the cells). In step 520, the plan is continued. For example, the introduction procedure is initiated (e.g., the injection), leading to the first time unit of the planned flow of the introduced entities. The system also verifies through imaging that the introduction device or devices have been placed within tolerance of the introduction sites called for by the plan. In addition, the system calls for user approval for go-ahead. At the first, least detailed level of control, such approval may be based simply on avoidance of clearly unfavorable areas that may otherwise be selected. Such unfavorable areas can be signaled by the computer based on processing of some image data. For example, avoiding introducing materials into a region that provides fast channels of flow into the ventricles, because that is not where they are needed. With such approval, the user (or system) introduces the material with numerical control of timing and pressure. As each time unit is completed, in step 520, it is determined whether the end of the plan has been completed. If it has, the injection procedure ends in step 575, with continued monitoring until the transport speed of the injected material has become negligible. If not, the image guidance system monitors the concentrations in step 525 and the computer compares the values with those predicted to see if there is a deviation in step 530. For example, in step 525, the system uses imaging to track the transport and where possible the activity of the introduced materials. Then, in step 530, where such imaging reveals divergence from the plan, it assesses the impact on the goals input by the user, and where necessary and possible computes a modified plan in real time to bring results closer to the specified ones, or at least avoiding the pre-specified exclusions or reducing the extent to which said limits are transgressed, and including in its computations the option of aborting the process. It offers such modified plans to the user, who can either execute them, instruct the system to do so, or collaborate with the system in doing so where (for example) new introduction materials must be loaded, or the introduction device moved. If the answer to step 530 is NO, and if disagreement is within a pre-set tolerance, the procedure reverts back to step 515 and repeats. If the answer to step 530 is YES, and if it exceeds this tolerance, the computer modifies parameter estimates in the light of the new data in step 535, and computes new predictions in step 540 with specifications of their confidence level.

In step 545, a determination is made as to whether the predictions of step 540 are acceptable. If the answer to step 545 is YES (i.e., the predictions are acceptable), the process moves to step 575 and ends. If the answer to step 545 is NO (i.e., the predictions are not acceptable), the process goes to step 550 to determine if there is time to prepare a satisfactory revised strategy. If the answer to step 550 is NO, and if there is not time, the process moves to the end step 575. If the answer to step 550 is YES, and if revision is practical, the user or the computer specifies a modification of the plan in step 555. The results are computed in step 560. In step 565, a determination is made as to whether the tests are acceptable. If the answer to step 565 is YES (i.e., the tests are acceptable) the procedure returns to step 515 and the process is repeated with the revised plan. If the answer to step 565 is NO (i.e., the test are not acceptable), in step 570 a determination is made as to whether enough time remains to complete the procedure. If the answer to step 570 is NO (i.e., time is not available), the process proceeds to step 575. If the answer to step 570 is YES (i.e., time is available), the search for an improved plan continues with a return to step 555. These loops continue until the end process of step 575 is reached.

Alternate Embodiment

Figure 6:
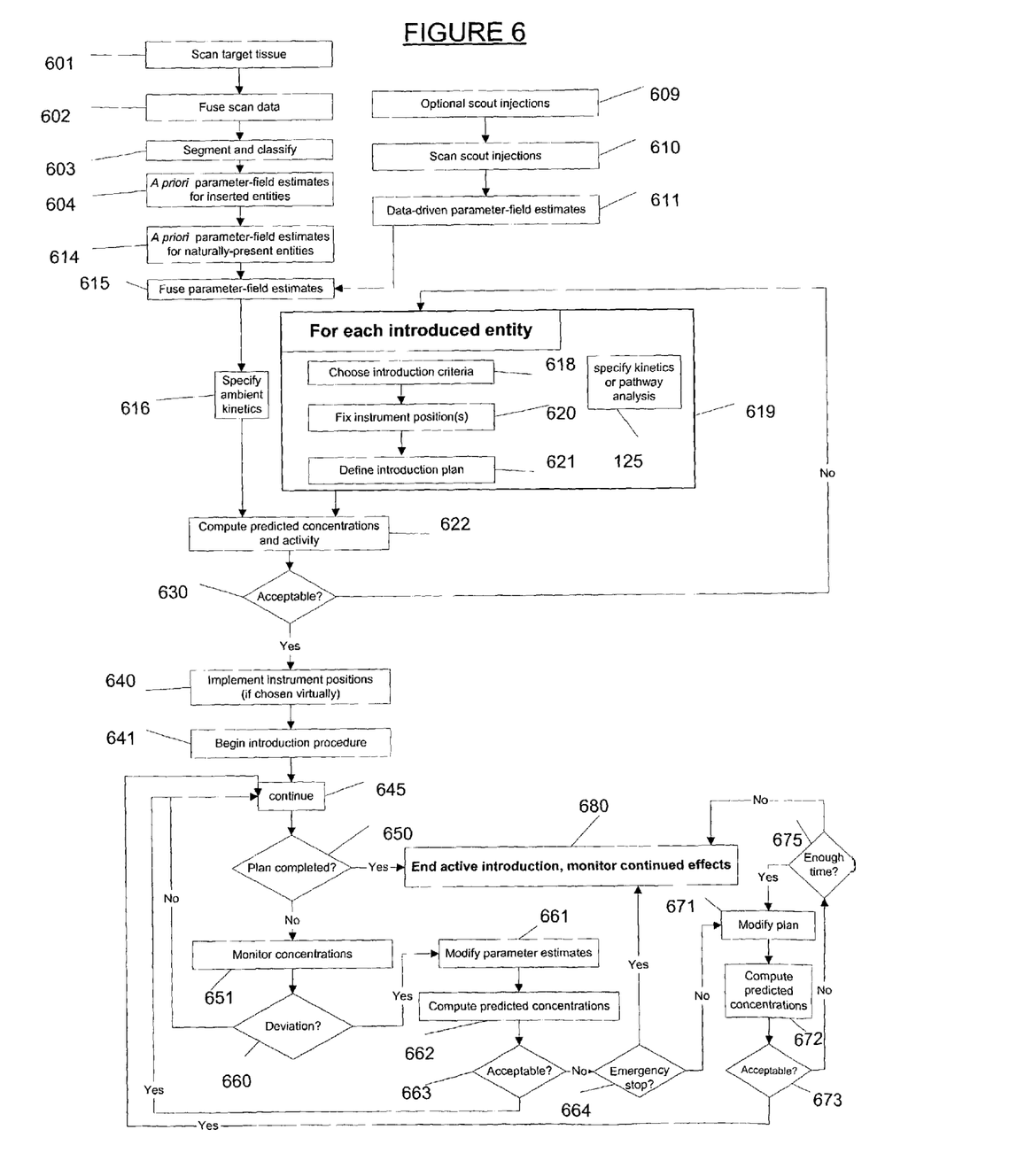
FIG. 6 is a flowchart illustrating an alternative embodiment of the present invention.

FIG. 6 is a flowchart illustrating an alternative embodiment of the present invention. In 601, the target tissue is scanned, using one or more 3D imaging modalities such as CAT, ultrasound, functional magnetic resonance, etc. For more than one modality, in 602 the data may be brought into a shared coordinate frame. Using the resulting information about tissue properties at each point in the scanned region, in 603 the points are classified into tissue types and assigned transport parameter values for the entities to be introduced (604) and those naturally present which play a role in the model (614) according to the general properties of these types. In some cases this provides sufficient information about transport properties in such tissue of the entity to be introduced, but commonly the user will also perform scout introductions (609) and scan the resulting changes in concentration of the same or a similar material (610), and thereby derive (611) estimates more specific to the patient, for the subregions in which the scout injections provide robust data, as attested by low measures of noise. These two estimations of parameter fields are merged (615), each point's parameter values being more strongly influenced by the more confidently derived estimate at that point, and sharp changes being more acceptable where there is evidence (from any modality) of a boundary. At this point or an earlier one, the user specifies the ambient kinetic model (616) for the interaction of the introduced transportable entities and optionally of entities naturally present.

The planning specific to the introduction begins with choosing regions that should receive the introduced entities, or that are vulnerable to them (618), and limits on allowable pressure and edema. This selection process may be in the mind of the user, setting the mental stage for later decisions, or input to the computer by means of a graphical interface. The user or in some implementations the computer then fixes (619) for each transportable material to be introduced a metabolic model (625) (trivial for a single compound or heat, etc., complex for a cell), and a position for each instrument to be used (620), which at this stage may be either a physical image-guided process or a virtual placement within a displayed scan image, internal to the subject (as, for injection), applied to the subject (as, for transdermal perfusion), or external to the subject (as, for radiative transmission). In 621, the user or the computer specifies quantity, duration, and pressure/flow-rate if the introduction is by injection, perfusion or the like, beam settings, strengths, duration, etc., if the introduction is radiative, and in 622, the computer predicts the resulting time course of concentrations or their possible range, and the activities of the introduced entities, using the transport parameters established in 615 and the metabolic models introduced in 616 and 625.

The user or the computer inspects the predicted values and, in 630, determines whether these are acceptable in the light of the injection goals. If no, the procedure returns to 619, where the instrument position may be readjusted, and in 621, defines new values for quantity, duration, pressure/flow-rate of the injection. If yes, in 640, the physical procedure begins: if the position was chosen virtually, the instrument must first be placed there physically.

641 initiates the injection proper, leading to, in 645, the first time unit (next after none) of the planned flow of the introduced entities. As each time unit is completed, in 650, a counter tests whether the end of the plan has been reached. If it has, the injection procedure ends in 680, with continued monitoring until the transport speed of the injected material has become negligible. If not, the image guidance system monitors the concentrations in 651, and the computer compares the values with those predicted in 660. If disagreement is within a pre-set tolerance, in 645, the procedure goes to the next time-step in the introduction plan. If it exceeds this tolerance, in 661, the computer revises parameter estimates in the light of the new data, and in 662, makes new predictions with specifications of their confidence level. If these are unacceptable and there is not the time to prepare a satisfactory revised strategy, in 663, a test diverts the procedure to end (680). If revision is practical, the user or the computer specifies a modification of the plan (671), computes the results (672) and tests (673) their acceptability. If they are satisfactory, in 645, the procedure continues with the revised plan. If not, in 675, the system decides whether time is running out. If it is, it goes to the end process in 680. If time is available, the search for an improved plan continues with a return to 671. These loops continue until the end process is reached in 680.

The method of design of the release of the transportable entity from the medical device may be based upon many different release structures or mechanisms. The release may be through actual holes or apertures in a cover for a lumen or on a catheter, membranes on a catheter, open/close stops or blocks on lumens in a catheter, electromagnetic or ultrasound radiation from an appropriate device internal or external to the subject, devices to extract blood and return it with a different temperature and/or different concentration of some compound, and the like. Each of these different types of systems will provide release or delivery characteristics that should be considered in the analysis of the delivery rate profiles in the practice of the invention.

Conclusion

The computations described above can be accomplished by the methods and systems herein described or by such other numerical solution methods as are known, or become known to those skilled in the art. The present invention is extremely computation-intensive, and thus dedicated, optimized hardware is helpful for its implementation in one embodiment. In an alternative embodiment, early implementations can simplify the cellular kinetics (e.g., reduction to an "equation of state" describing the equilibria of the system without the capacity to analyze the transients that are revealed by a full account of the chemical kinetics), until more powerful hardware becomes available through computer development. In an additional embodiment, the present invention may be utilized in the study of a number of trial subjects and parameter settings, with the results summarized in a system of guidelines. For example, for a patient with certain characteristics (e.g., height, weight, blood test result values, estimated distance between relevant brain landmarks), a specific set of guidelines can be provided (e.g., doses, input points, temperatures, and timing, as given by a table, a system of formulas, or a learning system such as a neural network that has been trained on the research subjects).

Where the system is used with a computer capable of carrying out multiple predictive simulations of transport in available time, the computer may search the space of possible plans for the plan with the result most quantitatively desirable according to the user-specified result. For example, the computer may begin with a heuristically chosen starting plan (e.g., a standard plan), investigate the predicted result of successive changes in the plan, make changes with improved results, and choose a plan whose results are within user-specified limits. Such a plan may be presented to the user, to be accepted or rejected. In another embodiment of the present invention, the user may quantitatively modify the plan, view the consequences of the modified plan, and select among this larger set.

As noted above, in one embodiment of the present invention, the results of a research program using the several levels of control described above may be summarized in customizable guidelines for the user of an introduction procedure studied by virtue of the simulations here described, which may be executed in the absence of a full simulation of the individual subject. In a further embodiment, the invention disclosed in "Targeting", expanded as in the present disclosure to a plurality of transportable entities introduced at a plurality of times, may be used to supervise whether the concentrations in such a customized procedure stay within acceptable limits, without requiring that the system also computes interaction kinetics in real time.

Example embodiments of the present invention have now been described in accordance with the above advantages. It will be appreciated that these examples are merely illustrative of the invention. Many variations and modifications will be apparent to those skilled in the art.

What is claimed is:

1. A computer-assisted method for determining at least one manner of introducing and moving at least one introduced entity from an at least one introduction site to at least one target tissue region in an organism, the method comprising:
receiving data representing a property of i) the at least one introduced entity, ii) the at least one introduction site, iii) the at least one target tissue region, iv) at least one pathway to the target tissue region, and/or iv) a device used to introduce the at least one entity;
calculating, from the received data, at least one modeling value at i) the at least one introduction site, ii) at least one pathway to the target tissue region, and iii) the at least one target tissue region;
calculating at least one diffusion value representing a concentration gradient of the at least one introduced entity as it moves through the introduction site, the pathway, and the target tissue region;
calculating at least one normal flow characteristic of at least one entity normally present in the organism;
determining, using a processor, a plan for intraparenchymally introducing and moving the at least one introduced entity based on the at least one modeling value, the at least one diffusion value, and the at least one normal flow characteristic;
calculating at least one biologically active transport value representing how the at least one introduced entity is transported through the introduction site, the pathway, and the target tissue region; and
outputting from the computer data showing how the at least one entity is transported through the at least one introduction site, the pathway, and the target tissue region.

2. The method of claim 1, wherein the plan comprises:
at least one time;
at least one location; and
at least one method.

3. The method of claim 2, wherein the at least one time, location, and method is determined by using modeling, biological activity, diffusion, and flow values of a representative organism with characteristics similar to the organism.

4. The method of claim 1, wherein the at least one introduced entity comprises at least one selected from a group consisting of:
at least one cellular material;
at least one non-cellular material; and
at least one electromagnetic stimulus.

5. The method of claim 4, wherein the at least one non-cellular material comprises at least one selected from a group consisting of:
hormones;
recombinant peptides;
neuropeptides;
trophic factors;
tropic factors;
interleukins;
cytokines;
colony stimulating factors;
caspase;
marker molecules; and
drugs.

6. The method of claim 1, wherein the organism comprises at least one selected from a group consisting of:
a human; and
a non-human mammal.

7. The method of claim 1, further comprising introducing the at least one entity according to the plan, wherein the at least one introduced entity moves through the organism to achieve at least one desired goal.

8. The method of claim 7, wherein the at least one desired goal comprises at least one selected from a group consisting of:
at least one therapeutic effect;
at least one cosmetic effect;
at least one modification of performance in at least one mental activity;

at least one modification of performance in at least one physical activity;
at least one measure of a secretion rate;
at least one measure of revascularization;
at least one measure of neural function;
at least one measure of muscular function;
at least one measure of tendon function;
at least one measure of bone quality and shape;
at least one measure of immunological function;
at least one measure of an effect of the at least one material on at least one cancer cell;
at least one measure of an effect of the at least one material on at least one fat cell;
at least one measure of an effect of the at least one material on an extracellular matrix;
at least one measure of an effect of the at least one material on at least one membrane;
at least one measure of an effect of the at least one material on lung tissue function; and
at least one measure of an effect of the at least one material on cardiac function.

9. The method of claim 1, wherein the introduction site, the pathway, and the target tissue region are modeled as a field of more than one point representing a property.

10. The method of claim 9, wherein the property comprises at least one selected from a group consisting of:
three-dimensional information;
at least one property of a device used to introduce the entity;
at least one value for an amount of the at least one introduced entity;
at least one value for at least one already-present entity; and
at least one value for at least one introduced scout entity.

11. The method of claim 1, wherein the at least one introduced entity is reintroduced and moved a plurality of times following a numerical specification.

12. The method of claim 11, wherein the numerical specification utilizes standard clinical parameters.

13. The method of claim 11, wherein the numerical specification is electrophysiologic from at least one of a group consisting of:
transcranial stimulation; and
intra-parenchymal electromagnetic stimulation.

14. The method of claim 1, further comprising:
calculating at least one biological activity value representing an interaction between the at least one introduced entity and the introduction site, the pathway, and the target tissue region; wherein determining a plan for introducing and moving the at least one introduced entity is based on the at least one modeling value, the at least one biological activity value, the at least one diffusion value, and the at least one flow value.

15. The method of claim 14, wherein the at least one time, location, and method is determined by using modeling, biological activity, diffusion, and flow values actually taken from the organism.

16. The method of claim 14, wherein the at least one biological activity value comprises at least one selected from a group consisting of:
dominant biochemical pathways;
blood flow;
functional magnetic resonance imaging;
a positron emission tomography (PET) scan;
electrical membrane potentials; and
cellular electrophysiologic activity.

17. The method of claim 1, wherein the at least one modeling value comprises at least one selected from a group consisting of:
functional capillary density;
tissue diffusion rate;
perfusion index;
histological configuration; and
extracellular matrix density.

18. The method of claim 1, wherein the at least one diffusion value comprises at least one selected from a group consisting of:
native cell density;
capillary density;
metabolites;
metabolic intermediates;
lymphatic capillary density; and
Cationic pump rate.

19. The method of claim 1, wherein the at least one transport value comprises at least one selected from a group consisting of:
at least one flow property of the at least one introduced entity;
at least one mobility property descriptive of entity mobility in the presence of the at least one introduced entity and its gradient; and
at least one metabolic pathway model for the at least one introduced entity, capable of yielding the at least one mobility property.

20. The method of claim 19, wherein the at least one metabolic pathway model comprises a metabolic pathway model for at least one already-present entity.

21. The method of claim 1, further comprising simulating movement of the at least one introduced entity.

22. The method of claim 21, wherein simulating movement of the at least one introduced entity comprises:
constructing at least one local physical quantity corresponding to at least one motion, appearance, and disappearance of the at least one introduced entity;
modeling at least one direction value to simulate the direction of motion of the at least one introduced entity;
computing at least one direction value over time; and
modeling at least one metabolic interaction of an already-present entity with the at least one introduced entity.

23. The method of claim 22, wherein simulated movement of the at least one introduced entity comprises at least one selected from a group consisting of:
optimizing resulting concentrations at the at least one target tissue area; and
minimizing resulting concentrations at areas that are not the at least one target tissue area.

24. The method of claim 22, further comprising:
modifying the at least one local physical quantity by at least one formula describing the at least one local physical quantity's change in response to at least one concentration of the introduced entity.

25. The method of claim 24, further comprising computing the at least one concentration by:
solving a finite differential equation constructed from a consortium model.

26. The method of claim 25, wherein the consortium model comprises:
at least one transport process.

27. The method of claim 25, wherein the consortium model comprises:
at least one absorption process.

28. The method of claim 25, wherein the consortium model comprises:
  at least one creation process.

29. The method of claim 25, wherein the consortium model comprises:
  at least one destruction process.

30. The method of claim 25, further comprising:
  comparing a predicted concentration to an actual measured concentration to modify the field of the at least one local physical quantity.

31. The method of claim 24, further comprising computing the at least one concentration by:
  utilizing at least one processor to handle a sub-region of the simulated volume; and
  using shared or separate memory of the field of local physical quantities.

32. The method of claim 24, further comprising computing the at least one concentration by:
  computing the motion of at least one simulated particle of said entity, with probability of motion in a particular direction controlled by a diffusion or conduction tensor field and probability of absorption, creation or destruction controlled by other parts of the field of local physical quantities.

33. The method of claim 24, further comprising computing the at least one concentration by:
  utilizing at least one processor to handle a sub-population of at least one simulated particle, and at least some of said multiplicity of processors using shared or separate memory of the field of local physical quantities.

34. The method of claim 33, wherein the at least one processor is embedded on at least one chip.

35. The method of claim 24, where the at least one concentration is graphically displayed.

36. The method of claim 22, wherein the at least one local physical quantity comprises at least one transport value descriptive of resistance to motion in different directions.

37. The method of claim 36, wherein the at least one transport value is descriptive of at least one selected from a group consisting of:
  cell mobility;
  conduction;
  diffusion; and
  flow property.

38. The method of claim 37, wherein the diffusion is selected from a group consisting of:
  concentrations; and
  motions.

39. The method according to claim 38, wherein the at least one diffusion value is known from actual measurements on other subjects.

40. The method of claim 21, wherein the at least one local physical quantity comprises at least one selected from a group consisting of:
  cell mobility;
  conduction;
  diffusion;
  flow;
  creation;
  destruction of molecules; and
  absorption.

41. The method of claim 40, wherein the at least one transport value is constructed from data of a scout entity that has at least one property similar to a property of the introduced entity.

42. The method according to claim 41, wherein the scout entity is constructed from at least one of a group consisting of:
  magnetic resonance data;
  data recorded from at least one previous introduction of the at least one introduced entity; and
  data permitting segmentation of the target tissue region into anatomical types, wherein at least one diffusion value is known.

43. The method of claim 41, wherein the scout entity comprises at least one of a group consisting of:
  a physical property; and
  a chemical property.

44. The method of claim 1, further comprising:
  specifying a target minimum or maximum of the introduced entity at the at least one target tissue region; and
  issuing a warning if the target minimum or maximum are predicted to be unmet using a planned time, location, and method.

45. The method of claim 1, further comprising exploring a range of possible planned times, locations, and methods and identifying preferential planned times, locations, and methods.

46. The method of claim 1, wherein a part of the target tissue region is displayed.

47. The method of claim 46, wherein at least one optical property relative to the target tissue region is visualized.

48. The method of claim 1, wherein the at least one entity comprises a cellular material.

49. A method for intraparenchymally administering at least one introduced entity to at least one target tissue region in an organism, the method comprising:
  introducing the at least one introduced entity in at least one intraparenchymal introduction site apart from the target tissue region; and
  using active biological transport to move the at least one introduced entity from the at least one intraparenchymal introduction site to the at least one target tissue region.

50. The method of claim 49, wherein the at least one introduced entity comprises a plurality of introduced entities.

51. The method of claim 49, wherein the at least one introduced entity is introduced a plurality of times.

52. A method for intraparenchymally administering at least one introduced entity to at least one target tissue region in an organism, the method comprising:
  introducing the at least one introduced entity in at least one intraparenchymal introduction site apart from the target tissue region; and
  metabolically guiding the at least one introduced entity from the at least one intraparenchymal introduction site to the at least one target tissue region.

* * * * *